US012714540B2

(12) United States Patent
Derakhshan et al.

(10) Patent No.: US 12,714,540 B2
(45) **Date of Patent: *Aug. 25, 2026**

(54) MATCHING ASSETS IN 3D TREATMENT PLANS

(71) Applicant: Align Technology, Inc., San Jose, CA (US)

(72) Inventors: Mitra Derakhshan, Herndon, VA (US); Sophie Acker, Amsterdam (NL); Susanne Reichart, Amsterdam (NL)

(73) Assignee: ALIGN TECHNOLOGY, INC., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/357,854

(22) Filed: Jun. 24, 2021

(65) Prior Publication Data

US 2022/0015867 A1 Jan. 20, 2022

Related U.S. Application Data

(63) Continuation of application No. 15/385,262, filed on Dec. 20, 2016, now Pat. No. 11,071,608.

(51) Int. Cl.

| | |
|---|---|
| ***A61C 7/00*** | (2006.01) |
| ***A61C 7/08*** | (2006.01) |
| ***G16H 20/30*** | (2018.01) |
| ***G16H 50/20*** | (2018.01) |

(52) U.S. Cl.

CPC ............. *A61C 7/002* (2013.01); *G16H 20/30* (2018.01); *G16H 50/20* (2018.01); *A61C 7/08* (2013.01)

(58) Field of Classification Search

CPC .......... A61C 7/002; A61C 7/08; G16H 20/30; G16H 50/20

See application file for complete search history.

(56) References Cited

U.S. PATENT DOCUMENTS

| | | | |
|---|---|---|---|
| 5,975,893 | A | 11/1999 | Chishti et al. |
| 6,227,850 | B1 | 5/2001 | Chishti et al. |
| 6,227,851 | B1 | 5/2001 | Chishti et al. |
| 6,299,440 | B1 | 10/2001 | Phan et al. |
| 6,309,215 | B1 | 10/2001 | Phan et al. |
| 6,318,994 | B1 | 11/2001 | Chishti et al. |
| 6,371,761 | B1 | 4/2002 | Cheang et al. |
| 6,386,878 | B1 | 5/2002 | Pavlovskaia et al. |
| 6,406,292 | B1 | 6/2002 | Chishti et al. |

(Continued)

*Primary Examiner* — Eric J Rosen
*Assistant Examiner* — Hao D Mai
(74) *Attorney, Agent, or Firm* — Wilson Sonsini Goodrich & Rosati

(57) ABSTRACT

A method for treating malocclusions of a patient's teeth is disclosed. The method includes receiving an initial position of a patient's teeth and a target position of the patient's teeth. The method also includes determining a treatment plan to reposition the patient's teeth towards the target position. The method also includes receiving treatment strategies for the patient's teeth based at least in part of the treatment plan and matching the initial position of the patient's teeth, the target position of a patient's teeth, and the treatment strategies for the patient's teeth with initial positions, target positions, and treatment strategies of a plurality of existing cases. The method also includes sending the matched cases to a dental practitioner including matched educational assets.

19 Claims, 8 Drawing Sheets

(56) References Cited

U.S. PATENT DOCUMENTS

| | | | |
|---|---|---|---|
| 6,409,504 | B1 | 6/2002 | Jones et al. |
| 6,450,807 | B1 | 9/2002 | Chishti et al. |
| 6,457,972 | B1 | 10/2002 | Chishti et al. |
| 6,488,499 | B1 | 12/2002 | Miller |
| 6,514,074 | B1 | 2/2003 | Chishti et al. |
| 6,554,611 | B2 | 4/2003 | Chishti et al. |
| 6,582,229 | B1 | 6/2003 | Miller et al. |
| 6,602,070 | B2 | 8/2003 | Miller et al. |
| 6,621,491 | B1 | 9/2003 | Baumrind et al. |
| 6,688,886 | B2 | 2/2004 | Hughes et al. |
| 6,726,478 | B1 | 4/2004 | Isiderio et al. |
| 6,729,876 | B2 | 5/2004 | Chishti et al. |
| 6,739,869 | B1 | 5/2004 | Taub et al. |
| 6,767,208 | B2 | 7/2004 | Kaza |
| 6,783,360 | B2 | 8/2004 | Chishti |
| 6,830,450 | B2 | 12/2004 | Knopp et al. |
| 7,040,896 | B2 | 5/2006 | Pavlovskaia et al. |
| 7,063,532 | B1 | 6/2006 | Jones et al. |
| 7,074,038 | B1 | 7/2006 | Miller |
| 7,074,039 | B2 | 7/2006 | Kopelman et al. |
| 7,077,647 | B2 | 7/2006 | Choi et al. |
| 7,108,508 | B2 | 9/2006 | Hedge et al. |
| 7,134,874 | B2 | 11/2006 | Chishti et al. |
| 7,156,661 | B2 | 1/2007 | Choi et al. |
| 7,160,107 | B2 | 1/2007 | Kopelman et al. |
| 7,241,142 | B2 | 7/2007 | Abolfathi et al. |
| 7,293,988 | B2 | 11/2007 | Wen |
| 7,309,230 | B2 | 12/2007 | Wen |
| 7,357,634 | B2 | 4/2008 | Knopp |
| 7,555,403 | B2 | 6/2009 | Kopelman et al. |
| 7,637,740 | B2 | 12/2009 | Knopp |
| 7,689,398 | B2 | 3/2010 | Cheng et al. |
| 7,736,147 | B2 | 6/2010 | Kaza et al. |
| 7,746,339 | B2 | 6/2010 | Matov et al. |
| 7,844,356 | B2 | 11/2010 | Matov et al. |
| 7,844,429 | B2 | 11/2010 | Matov et al. |
| 7,865,259 | B2 | 1/2011 | Kuo et al. |
| 7,878,804 | B2 | 2/2011 | Korytov et al. |
| 7,880,751 | B2 | 2/2011 | Kuo et al. |
| 7,904,308 | B2 | 3/2011 | Arnone et al. |
| 7,930,189 | B2 | 4/2011 | Kuo |
| 7,942,672 | B2 | 5/2011 | Kuo |
| 7,970,627 | B2 | 6/2011 | Kuo et al. |
| 7,970,628 | B2 | 6/2011 | Kuo et al. |
| 8,038,444 | B2 | 10/2011 | Kitching et al. |
| 8,044,954 | B2 | 10/2011 | Kitching et al. |
| 8,075,306 | B2 | 12/2011 | Kitching et al. |
| 8,092,215 | B2 | 1/2012 | Stone-Collonge et al. |
| 8,099,268 | B2 | 1/2012 | Kitching et al. |
| 8,108,189 | B2 | 1/2012 | Chelnokov et al. |
| 8,126,726 | B2 | 2/2012 | Matov et al. |
| 8,260,591 | B2 | 9/2012 | Kass et al. |
| 8,275,180 | B2 | 9/2012 | Kuo |
| 8,401,826 | B2 | 3/2013 | Cheng et al. |
| 8,439,672 | B2 | 5/2013 | Matov et al. |
| 8,562,338 | B2 | 10/2013 | Kitching et al. |
| 8,591,225 | B2 | 11/2013 | Wu et al. |
| 8,788,285 | B2 | 7/2014 | Kuo |
| 8,843,381 | B2 | 9/2014 | Kuo et al. |
| 8,874,452 | B2 | 10/2014 | Kuo |
| 8,896,592 | B2 | 11/2014 | Boltunov et al. |
| 8,930,219 | B2 | 1/2015 | Trosien et al. |
| 9,037,439 | B2 | 5/2015 | Kuo et al. |
| 9,060,829 | B2 | 6/2015 | Sterental et al. |
| 9,125,709 | B2 | 9/2015 | Matty |
| 9,211,166 | B2 | 12/2015 | Kuo et al. |
| 9,220,580 | B2 | 12/2015 | Borovinskih et al. |
| 9,364,296 | B2 | 6/2016 | Kuo |
| 9,375,300 | B2 | 6/2016 | Matov et al. |
| 9,414,897 | B2 | 8/2016 | Wu et al. |
| 9,492,245 | B2 | 11/2016 | Sherwood et al. |
| 9,642,678 | B2 | 5/2017 | Kuo |
| 10,248,883 | B2 | 4/2019 | Borovinskih et al. |
| 10,342,638 | B2 | 7/2019 | Kitching et al. |
| 10,463,452 | B2 | 11/2019 | Matov et al. |
| 10,595,966 | B2 | 3/2020 | Carrier, Jr. et al. |
| 10,617,489 | B2 | 4/2020 | Grove et al. |
| 10,722,328 | B2 | 7/2020 | Velazquez et al. |
| 10,758,322 | B2 | 9/2020 | Pokotilov et al. |
| 10,779,718 | B2 | 9/2020 | Meyer et al. |
| 10,792,127 | B2 | 10/2020 | Kopelman et al. |
| 10,828,130 | B2 | 11/2020 | Pokotilov et al. |
| 10,835,349 | B2 | 11/2020 | Cramer et al. |
| 10,973,611 | B2 | 4/2021 | Pokotilov et al. |
| 10,996,813 | B2 | 5/2021 | Makarenkova et al. |
| 10,997,727 | B2 | 5/2021 | Xue et al. |
| 11,020,205 | B2 | 6/2021 | Li et al. |
| 11,020,206 | B2 | 6/2021 | Shi et al. |
| 11,026,766 | B2 | 6/2021 | Chekh et al. |
| 11,033,359 | B2 | 6/2021 | Velazquez et al. |
| 11,096,763 | B2 | 8/2021 | Akopov et al. |
| 11,116,605 | B2 | 9/2021 | Nyukhtikov et al. |
| 11,147,652 | B2 | 10/2021 | Mason et al. |
| 11,151,753 | B2 | 10/2021 | Gao et al. |
| 2003/0008259 | A1 | 1/2003 | Kuo et al. |
| 2003/0143509 | A1 | 7/2003 | Kopelman et al. |
| 2003/0207227 | A1 | 11/2003 | Abolfathi |
| 2004/0137400 | A1 | 7/2004 | Chishti et al. |
| 2004/0152036 | A1 | 8/2004 | Abolfathi |
| 2004/0197728 | A1 | 10/2004 | Abolfathi et al. |
| 2004/0259049 | A1 | 12/2004 | Kopelman et al. |
| 2005/0038669 | A1 * | 2/2005 | Sachdeva ............... G06Q 50/22 705/2 |
| 2005/0182654 | A1 | 8/2005 | Abolfathi et al. |
| 2005/0244791 | A1 | 11/2005 | Davis et al. |
| 2006/0127836 | A1 | 6/2006 | Wen |
| 2006/0127852 | A1 | 6/2006 | Wen |
| 2006/0127854 | A1 | 6/2006 | Wen |
| 2006/0275731 | A1 | 12/2006 | Wen et al. |
| 2006/0275736 | A1 | 12/2006 | Wen et al. |
| 2008/0306724 | A1 | 12/2008 | Kitching et al. |
| 2009/0132455 | A1 * | 5/2009 | Kuo ......................... A61C 7/00 706/46 |
| 2010/0009308 | A1 | 1/2010 | Wen et al. |
| 2010/0068672 | A1 | 3/2010 | Arjomand et al. |
| 2010/0068676 | A1 | 3/2010 | Mason et al. |
| 2010/0092907 | A1 | 4/2010 | Knopp |
| 2010/0167243 | A1 | 7/2010 | Spiridonov et al. |
| 2013/0204599 | A1 | 8/2013 | Matov et al. |
| 2016/0120617 | A1 * | 5/2016 | Jinkyun ................. A61B 6/032 433/29 |
| 2016/0242870 | A1 | 8/2016 | Matov et al. |
| 2016/0310235 | A1 | 10/2016 | Derakhshan et al. |
| 2017/0273760 | A1 | 9/2017 | Morton et al. |
| 2018/0280118 | A1 | 10/2018 | Cramer |
| 2019/0029784 | A1 | 1/2019 | Moalem et al. |
| 2019/0053876 | A1 | 2/2019 | Sterental et al. |
| 2019/0192259 | A1 | 6/2019 | Kopelman et al. |
| 2019/0328487 | A1 | 10/2019 | Levin et al. |
| 2019/0328488 | A1 | 10/2019 | Levin et al. |
| 2019/0333622 | A1 | 10/2019 | Levin et al. |
| 2019/0343601 | A1 | 11/2019 | Roschin et al. |
| 2020/0000552 | A1 | 1/2020 | Mednikov et al. |
| 2020/0000554 | A1 | 1/2020 | Makarenkova et al. |
| 2020/0000555 | A1 | 1/2020 | Yuryev et al. |
| 2020/0085546 | A1 | 3/2020 | Li et al. |
| 2020/0107915 | A1 | 4/2020 | Roschin et al. |
| 2020/0155274 | A1 | 5/2020 | Pimenov et al. |
| 2020/0214800 | A1 | 7/2020 | Matov et al. |
| 2020/0297458 | A1 | 9/2020 | Roschin et al. |
| 2020/0306011 | A1 | 10/2020 | Chekhonin et al. |
| 2020/0306012 | A1 | 10/2020 | Roschin et al. |
| 2020/0315744 | A1 | 10/2020 | Cramer |
| 2020/0360109 | A1 | 11/2020 | Gao et al. |
| 2021/0073998 | A1 | 3/2021 | Brown et al. |
| 2021/0134436 | A1 | 5/2021 | Meyer et al. |
| 2021/0174477 | A1 | 6/2021 | Shi et al. |

* cited by examiner

320

Apply a first orthodontic appliance to a patient's teeth to reposition the teeth from a first tooth arrangement to a second tooth arrangement

330

Apply a second orthodontic appliance to the patient's teeth to reposition the teeth from the second tooth arrangement to a third tooth arrangement

340

STORAGE SUBSYSTEM
706
708
MEMORY SUBSYSTEM
RAM
710
ROM
712
FILE STORAGE SUBSYSTEM
714
704
BUS SYSTEM
PROCESSOR(S)
702
NETWORK INTERFACE
716
USER INTERFACE AND OUTPUT DEVICE
718
SCANNER
720
NETWORK
724
FABRICATION MACHINE
722
CASTS
721
APPLIANCES
723

MATCHING ASSETS IN 3D TREATMENT PLANS

CROSS-REFERENCE

This application is a continuation of U.S. patent application Ser. No. 15/385,262, filed Dec. 20, 2016, now U.S. Pat. No. 11,071,608, issued Jul. 27, 2021, which is incorporated herein by reference in its entirety.

BACKGROUND

One objective of orthodontics is to realign patients' teeth to positions where the teeth function optimally and have an aesthetic appearance. The goal of a dental practitioner is to take the patient from their current condition also referred to as an initial or starting dentition, arrangement, or malocclusion to, or towards, a final condition, arrangement, or treatment goal. The result achieved is known as the treatment outcome. A dental practitioner has may have many alternative or complementary treatment options or strategies for a patient to move the patient's teeth towards the treatment goal. A treatment plan includes the various selected methodologies used by the dental practitioner to move the patient's teeth towards the treatment goal.

Typically, appliances such as fixed braces and wires are applied to a patient's teeth to gradually reposition them from an initial arrangement to a final arrangement. The diagnosis and treatment planning process of orthodontic cases can be imprecise as the final dentition of a patient is based on the knowledge and expertise of the treating dental practitioner in assembling various parameters in an assessment of each patient's condition and in a determination of a final position for each tooth. Different clinicians will vary in their definitions of individual orthodontic parameters and their definition of how a case should ideally be treated will also often vary.

Dental practitioners may use different methods of moving teeth towards a treatment goal, based on their personal past experiences with the various options for moving teeth from particular starting arrangement towards a particular desired final condition. Dental practitioners may be unware of or unfamiliar with some approaches for moving teeth because the approach is new, perceived as difficult, only applies is rarely encountered situations, or for other reasons.

In view of the foregoing, it would be desirable to have methods and systems for matching assets, such as existing cases, including past cases and presently pending cases, and educational materials to orthodontic assessments and treatment plans.

SUMMARY

Improved systems and methods for repositioning a patient's teeth are provided herein.

A method for treating malocclusions of a patient's teeth is disclosed. The method may comprise receiving an initial position of a patient's teeth; receiving a target position of the patient's teeth; determining a treatment plan to reposition the patient's teeth towards the target position; receiving treatment strategies for the patient's teeth based at least in part of the treatment plan; matching the initial position of the patient's teeth, the target position of a patient's teeth, and the treatment strategies for the patient's teeth with initial positions, target positions, and treatment strategies of a plurality of existing cases; and sending the matched cases to a dental practitioner.

In some embodiment the method may include receiving patient factors for the patient, wherein the matching comprises matching the patient factors for the patient with patient factors of the plurality of existing cases. The patient factors may include one or more of age, sex, ethnicity, and race. The patient factors may include one or more of tooth shape, tooth size, tooth morphology, and arch shape. The treatment strategies may include or more of tooth extraction, elastics use, attachment use, staging, and class II correction. The target position may be an intermediate position of the patient's teeth during treatment. The target position may be a desired position of the patient's teeth at the end of treatment.

The matching may include binary matching of at least one of the initial position of the patient's teeth, the target position of a patient's teeth, and the treatment strategies for the patient's teeth with initial positions, target positions, and treatment strategies of a plurality of existing cases. The matching may include matching includes determining a degree of match of at least one of the initial position of the patient's teeth, the target position of a patient's teeth, and the treatment strategies for the patient's teeth with initial positions, target positions, and treatment strategies of a plurality of existing cases. The matching may include matching includes averaging the degree of match of at least one of the initial position of the patient's teeth, the target position of a patient's teeth, and the treatment strategies for the patient's teeth with initial positions, target positions, and treatment strategies of a plurality of existing cases.

The method may include ranking the existing cases based on the matching. The ranking may include selecting existing cases based on their ranking and providing the selected existing cases to the dental professional. The method may include providing at least three cases from the five highest ranked existing cases and providing the three selected existing cases to the dental professional.

A method of treating malocclusions of a patient's teeth is disclosed. The method may comprise receiving initial and target positions of a patient's teeth; receiving treatment strategies for moving the patient's teeth from the initial position towards a target position; receiving patient factors; matching the initial position, target position, treatment strategies and patient factors with initial position, target position, treatment strategies and patient factors of existing cases; and providing the matching cases to a dental practitioner.

The method may include receiving patient factors for the patient, and wherein the matching comprises matching the patient factors for the patient with patient factors of the plurality of existing cases. The patient factors may include one or more of age, sex, ethnicity and race. The patient factors may include one or more of tooth shape, tooth size, tooth morphology, and arch shape. The treatment strategies may include or more of tooth extraction, elastics use, attachment use, staging, and class II correction. The target position is an intermediate position of the patient's teeth during treatment. The target position may be a desired position of the patient's teeth at the end of treatment.

The matching may include binary matching of at least one of the initial position of the patient's teeth, the target position of a patient's teeth, and the treatment strategies for the patient's teeth with initial positions, target positions, and treatment strategies of a plurality of existing cases. The matching includes matching may include determining a degree of match of at least one of the initial position of the patient's teeth, the target position of a patient's teeth, and the treatment strategies for the patient's teeth with initial positions, target positions, and treatment strategies of a plurality of existing cases. The matching includes matching may include averaging the degree of match of at least one of the initial position of the patient's teeth, the target position of a patient's teeth, and the treatment strategies for the patient's teeth with initial positions, target positions, and treatment strategies of a plurality of existing cases. The method may include raking the existing cases based on the matching.

The ranking may include selecting existing cases based on their ranking and providing the selected existing cases to the dental professional. The method may include providing at least three cases from the five highest ranked existing cases and providing the three selected existing cases to the dental professional.

In some aspects a method of treating malocclusions of a patient's teeth is disclosed. The method may comprise receiving initial and target positions of a patient's teeth; receiving treatment strategies for moving the patient's teeth from the initial position towards a target position; receiving dental practitioner factors of a dental practitioner; matching the initial position, target position, treatment strategies and patient factors with educational assets; and providing the educational assets to the dental practitioner.

The method may include receiving patient factors for the patient, and wherein the matching comprises matching the patient factors for the patient with patient factors of the plurality of existing cases. The patient factors may include one or more of age, sex, ethnicity, and race. The patient factors may include one or more of tooth shape, tooth size, tooth morphology, and arch shape. The treatment strategies may include or more of tooth extraction, elastics use, attachment use, staging, and class II correction. The target position may be an intermediate position of the patient's teeth during treatment. The target position may be a desired position of the patient's teeth at the end of treatment.

The matching may include binary matching of the initial position, target position, treatment strategies and patient factors with educational assets. The matching may include matching includes determining a degree of match of the initial position, target position, treatment strategies and patient factors with educational assets. The method may include raking the existing cases based on the matching. The method may include providing ranking includes selecting existing cases based on their ranking and providing the selected existing cases to the dental professional. The method may include providing at least three cases from the five highest ranked existing cases and providing the three selected existing cases to the dental professional.

In some aspects a system for treating malocclusions of a patient's teeth is disclosed. The system my comprise a receiver to receive an initial position of a patient's teeth and a target position of the patient's teeth; a processor configured to determine a treatment plan to reposition the patient's teeth towards the target position, determine treatment strategies for the patient's teeth based at least in part of the treatment plan, and match the initial position of the patient's teeth, the target position of a patient's teeth, and the treatment strategies for the patient's teeth with initial positions, target positions, and treatment strategies of a plurality of existing cases; and an interface configured to provide the matched cases to a dental practitioner. Other objects and features of the present disclosure will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
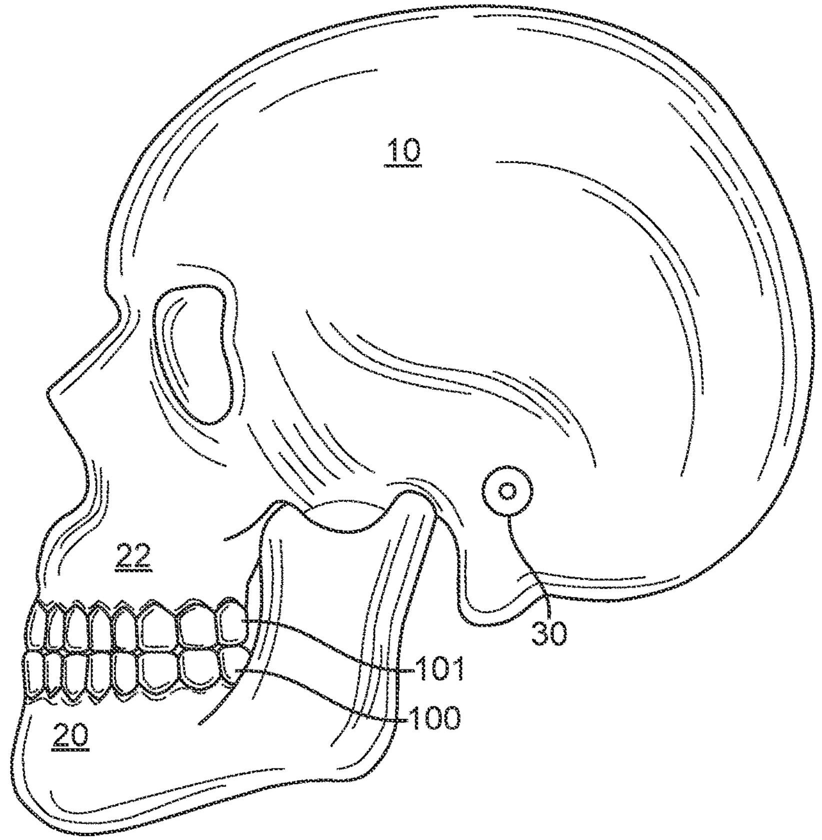
FIG. 1 is an elevational diagram showing the anatomical relationship of the jaws of a patient, in accordance with embodiments.

A better understanding of the features and advantages of the present disclosure will be obtained by reference to the following detailed description that sets forth illustrative embodiments, in which the principles of embodiments of the present disclosure are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the methods, systems, and apparatus of the present disclosure provided herein without departing from the spirit and scope of the disclosure as described herein.

As used herein the terms "dental appliance," "orthodontic appliance," and "tooth receiving appliance" are treated synonymously.

As used herein the term "and/or" is used as a functional word to indicate that two words or expressions are to be taken together or individually. For example, A and/or B encompasses A alone, B alone, and A and B together.

As used herein a "plurality of teeth" encompasses two or more teeth. In some embodiments, one or more posterior teeth comprises one or more of a molar, a premolar or a canine, and one or more anterior teeth comprising one or more of a central incisor, a lateral incisor, a cuspid, a first bicuspid or a second bicuspid.

The present disclosure provides orthodontic systems and related methods for providing improved or more effective tooth moving systems for eliciting a desired tooth movement and/or repositioning teeth into a desired arrangement.

The embodiments disclosed herein are well suited for combination with one or known commercially available tooth moving components such as attachments and polymeric shell appliances. In some embodiments, the appliance and one or more attachments are configured to move one or more teeth along a tooth movement vector comprising six degrees of freedom, in which three degrees of freedom are rotational and three degrees of freedom are translation.

The present disclosure provides orthodontic appliances and related systems, methods, and devices. Repositioning of teeth may be accomplished with the use of a series of removable elastic positioning appliances such as the Invisalign® system available from Align Technology, Inc., the assignee of the present disclosure. Such appliances may have a thin shell of elastic material that generally conforms to a patient's teeth but is slightly out of alignment with an initial or immediately prior tooth configuration. Placement of the appliance over the teeth applies controlled forces in specific locations to gradually move the teeth into the new configuration. Repetition of this process with successive appliances comprising new configurations eventually moves the teeth through a series of intermediate configurations or alignment patterns to a final desired configuration.

The force generating components disclosed herein can generate forces based on a target tooth displacement or orientation. For example, an amount of tooth displacement can be selected, and the force generating component can be fabricated such that a tooth displacement force is generated when the appliance is worn, so long as the amount of tooth displacement is less than the target tooth displacement. Thus, an appliance can generate tooth displacement forces without causing excessive tooth displacement. In some cases, the target tooth displacement can be adjustable; for example, adjustable screws, springs, bands, or other components can be adjusted to change the size of the aligner, thereby changing the target tooth displacement. An adjustable aligner can be used to generate a slow tooth displacement, for example.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication as described herein, for example. Alternatively or in combination, the appliance can be fabricated with machining such as an appliance fabricated from a block of material with computer numeric control machining.

Turning now to the drawings, FIG. 1 shows a skull 10 with an upper jawbone 22 and a lower jawbone 20. The lower jawbone 20 hinges at a joint 30 to the skull 10. The joint 30 is called a temporomandibular joint (TMJ). The upper jawbone 22 is associated with an upper jaw 101, while the lower jawbone 20 is associated with a lower jaw 100.

A computer model of the jaws 100 and 101 can be generated, and a computer simulation models interactions among the teeth on the jaws 100 and 101. The computer simulation can allow the system to focus on motions involving contacts between teeth mounted on the jaws. The computer simulation can allow the system to render realistic jaw movements which are physically correct when the jaws 100 and 101 contact each other. Further, the model can be used to simulate jaw movements including protrusive motions, lateral motions, and "tooth guided" motions where the path of the lower jaw 100 is guided by teeth contacts rather than by anatomical limits of the jaws 100 and 101. Motions can be determined for one jaw, but may also be determined for both jaws to represent the bite.

Figure 2A:
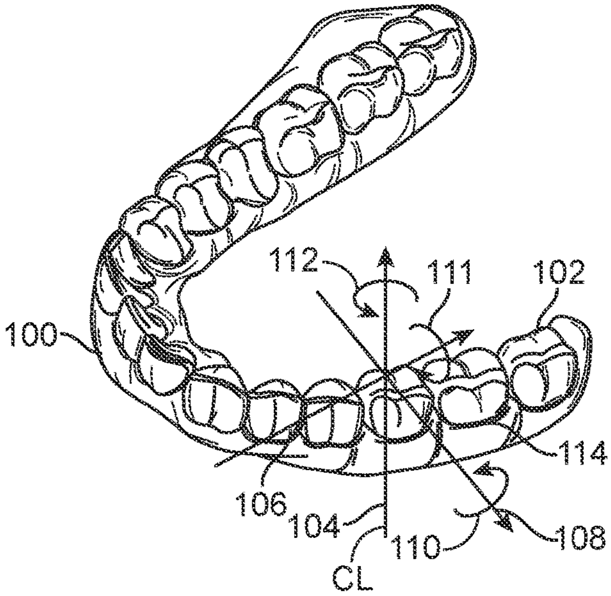
FIG. 2A shows in more detail the patient's lower jaw and provides a general indication of how teeth may move, in accordance with embodiments.

Referring now to FIG. 2A, the lower jaw 100 includes a plurality of teeth 102, for example. At least some of these teeth may be moved from an initial tooth arrangement to a subsequent tooth arrangement. As a frame of reference describing how a tooth has been moved, an arbitrary centerline (CL) may be drawn through the tooth 102. With reference to this centerline (CL), each tooth movement may be tracked in orthogonal directions represented by axes 104, 106, and 108 (where 104 is the centerline). The tooth may be rotated about the axis 108 (angulation), axis 106 (proclination), and the axis 104 (rotation) as indicated by arrows 110, 111, and 112, respectively. Additionally, the tooth may be rotated about the centerline. Thus, all possible free-form motions of the tooth can be tracked. These motions include translation (e.g., movement in one or more of the X-axis or Y-axis), rotation (e.g., movement about the Z-axis), intrusion and extrusion (e.g., movement in the Z-axis), or tipping (e.g., movement about one or more of the X-axis or Y-axis), to name a few. In addition to teeth movement, the movement of the gum line 114 may also be tracked using models such as model 100. In some embodiments, the model includes X-ray information of the jaw so that movements of the roots of the teeth can be tracked as well.

Figure 2B:
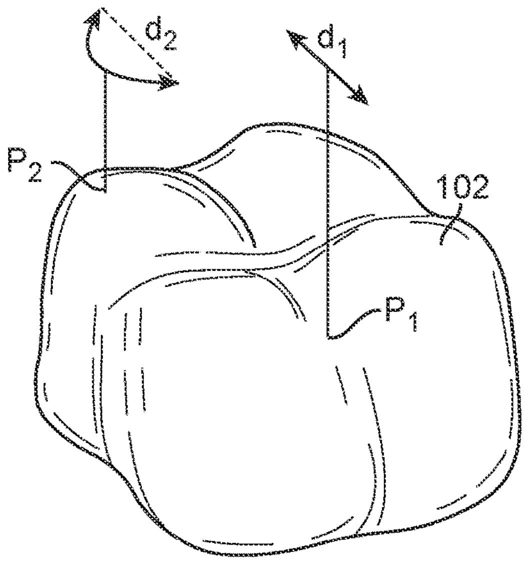
FIG. 2B shows a single tooth from FIG. 2A and defines how tooth movement distances can be determined, in accordance with embodiments.

FIG. 2B shows how the magnitude of any tooth movement may be defined in terms of a maximum linear translation of any point P on a tooth 102. Each point P1 may undergo a cumulative translation as that tooth is moved in any of the orthogonal or rotational directions defined in FIG. 2A. That is, while the point will usually follow a nonlinear path, there can be a linear distance between any point in the tooth when determined at any two times during the treatment. Thus, an arbitrary point P1 may in fact undergo a true side-to-side translation as indicated by arrow d1, while a second arbitration point P2 may travel along an arcuate path, resulting in a final translation d2. Many aspects of the present disclosure may be defined in terms of the maximum permissible movement of a point P1 induced on any particular tooth. Such maximum tooth movement, in turn, can be defined as the maximum linear translation of that point P1 on the tooth which undergoes the maximum movement for that tooth in any treatment step. In embodiments where the orthodontic treatment includes a temporal series of treatment steps, the tooth velocity can be defined as the maximum movement per treatment step. Each treatment step can be defined as the duration each orthodontic appliance is worn (e.g., 1 to 2 weeks).

Figure 3A:
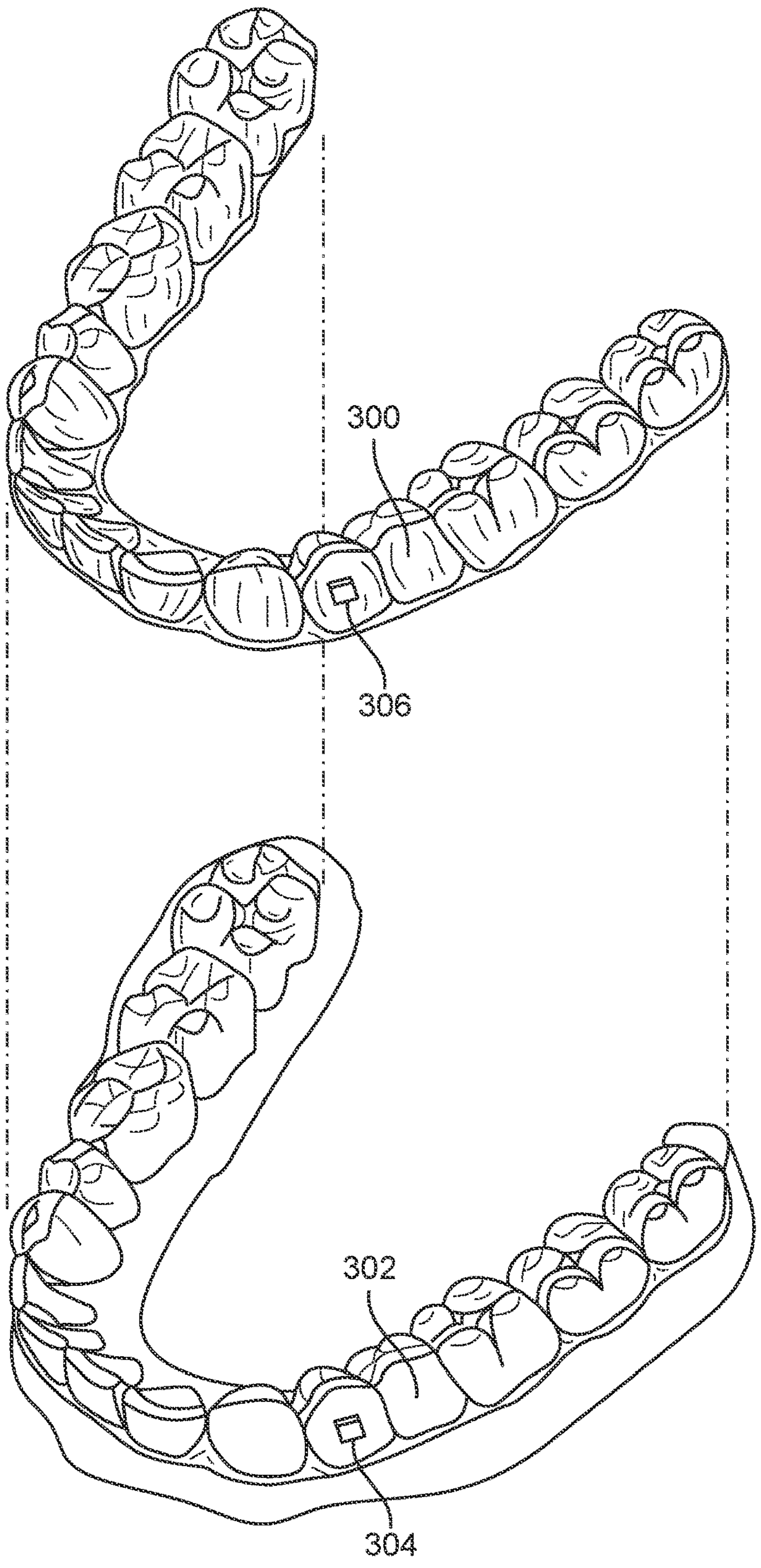
FIG. 3A illustrates a tooth repositioning appliance, in accordance with embodiments.

The present disclosure provides various orthodontic treatment procedures in which tooth movement is achieved through placement of one or more orthodontic appliances on a patient's teeth. Appliances having teeth receiving cavities that receive and reposition teeth, e.g., via application of force due to appliance resiliency, are generally illustrated with regard to FIG. 3A. FIG. 3A illustrates an exemplary tooth repositioning appliance or aligner 300 that can be worn by a patient in order to achieve an incremental repositioning of individual teeth 302 in the jaw. The appliance can include a shell having teeth-receiving cavities that receive and resiliently reposition the teeth. An appliance or portion(s) thereof may be indirectly fabricated using a physical model of teeth. For example, an appliance (e.g., polymeric appliance) can be formed using a physical model of teeth and a sheet of suitable layers of polymeric material. In some embodiments, a physical appliance is directly fabricated, e.g., using rapid prototyping fabrication techniques, from a digital model of an appliance.

Although reference is made to an appliance comprising a polymeric shell appliance, the embodiments disclosed herein are well suited for use with many appliances that receive teeth, for example appliances without one or more of polymers or shells. The appliance can be fabricated with one or more of many materials such as metal, glass, reinforced fibers, carbon fiber, composites, reinforced composites, aluminum, biological materials, and combinations thereof for example. The appliance can be shaped in many ways, such as with thermoforming or direct fabrication (e.g., 3D printing, additive manufacturing), for example. Alternatively or in combination, the appliance can be fabricated with machining such as an appliance fabricated from a block of material with computer numeric control machining.

An appliance can fit over all teeth present in an upper or lower jaw, or less than all of the teeth. The appliance can be designed specifically to accommodate the teeth of the patient (e.g., the topography of the tooth-receiving cavities matches the topography of the patient's teeth), and may be fabricated based on positive or negative models of the patient's teeth generated by impression, scanning, and the like. Alternatively, the appliance can be a generic appliance configured to receive the teeth, but not necessarily shaped to match the topography of the patient's teeth. In some cases, only certain teeth received by an appliance will be repositioned by the appliance while other teeth can provide a base or anchor region for holding the appliance in place as it applies force against the tooth or teeth targeted for repositioning. In some embodiments, some, most, or even all of the teeth will be repositioned at some point during treatment. Teeth that are moved can also serve as a base or anchor for holding the appliance as it is worn by the patient. Typically, no wires or other means will be provided for holding an appliance in place over the teeth. In some cases, however, it may be desirable or necessary to provide individual attachments or other anchoring elements 304 on teeth 302 with corresponding receptacles or apertures 306 in the appliance 300 so that the appliance can apply a selected force on the tooth. Exemplary appliances, including those utilized in the Invisalign® System, are described in numerous patents and patent applications assigned to Align Technology, Inc. including, for example, in U.S. Pat. Nos. 6,450,807, and 5,975,893, as well as on the company's website, which is accessible on the World Wide Web (see, e.g., the url "invisalign.com"). Examples of tooth-mounted attachments suitable for use with orthodontic appliances are also described in patents and patent applications assigned to Align Technology, Inc., including, for example, U.S. Pat. Nos. 6,309,215 and 6,830,450.

Figure 3B:
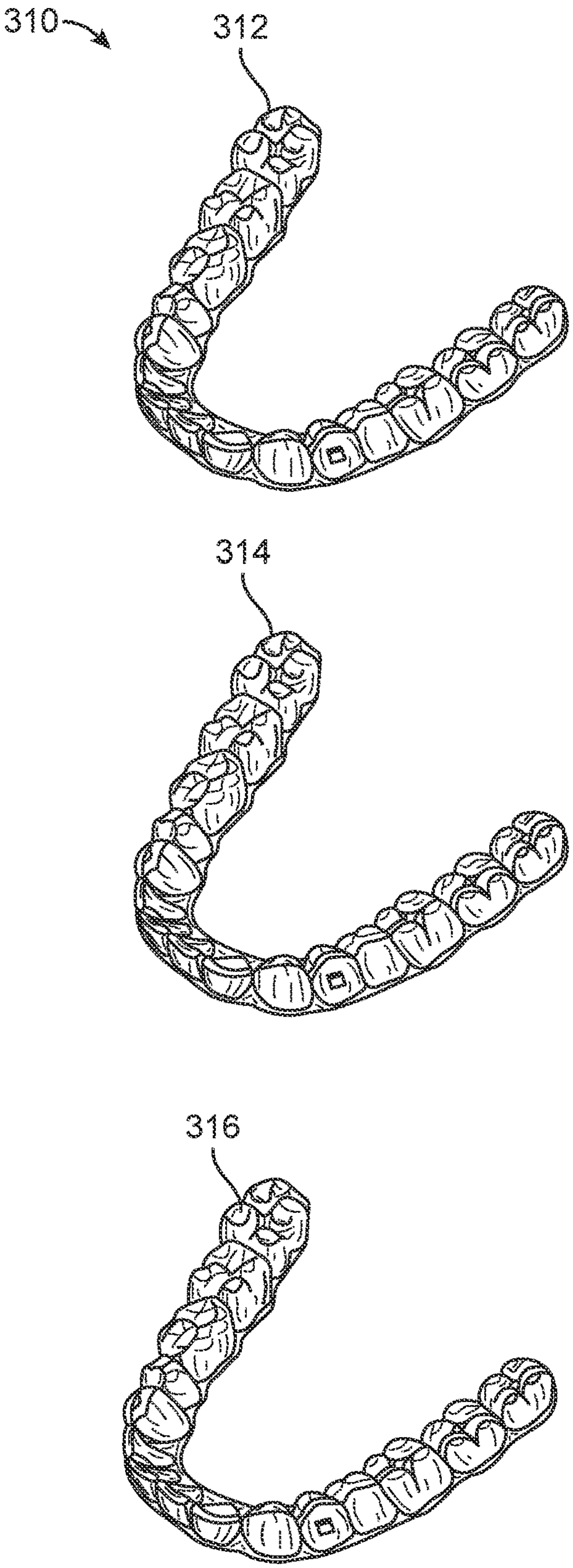
FIG. 3B illustrates a tooth repositioning system, in accordance with embodiments.

FIG. 3B illustrates a tooth repositioning system 310 including a plurality of appliances 312, 314, 316. Any of the appliances described herein can be designed and/or provided as part of a set of a plurality of appliances used in a tooth repositioning system. Each appliance may be configured so a tooth-receiving cavity has a geometry corresponding to an intermediate or final tooth arrangement intended for the appliance. The patient's teeth can be progressively repositioned from an initial tooth arrangement to a target tooth arrangement by placing a series of incremental position adjustment appliances over the patient's teeth. For example, the tooth repositioning system 310 can include a first appliance 312 corresponding to an initial tooth arrangement, one or more intermediate appliances 314 corresponding to one or more intermediate arrangements, and a final appliance 316 corresponding to a target arrangement. A target tooth arrangement can be a planned final tooth arrangement selected for the patient's teeth at the end of all planned orthodontic treatment. Alternatively, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

The various embodiments of the orthodontic appliances presented herein can be fabricated in a wide variety of ways. As an example, some embodiments of the appliances herein (or portions thereof) can be produced using indirect fabrication techniques, such as by thermoforming over a positive or negative mold. Indirect fabrication of an orthodontic appliance can involve producing a positive or negative mold of the patient's dentition in a target arrangement (e.g., by rapid prototyping, milling, etc.) and thermoforming one or more sheets of material over the mold in order to generate an appliance shell. Alternatively or in combination, some embodiments of the appliances herein may be directly fabricated, e.g., using rapid prototyping, stereolithography, 3D printing, and the like.

The configuration of the orthodontic appliances herein can be determined according to a treatment plan for a patient, e.g., a treatment plan involving successive administration of a plurality of appliances for incrementally repositioning teeth. Computer-based treatment planning and/or appliance manufacturing methods can be used in order to facilitate the design and fabrication of appliances. For instance, one or more of the appliance components described herein can be digitally designed and fabricated with the aid of computer-controlled manufacturing devices (e.g., computer numerical control (CNC) milling, computer-controlled rapid prototyping such as 3D printing, etc.). The computer-based methods presented herein can improve the accuracy, flexibility, and convenience of appliance fabrication.

In some embodiments, orthodontic appliances, such as the appliance illustrated in FIG. 3A, impart forces to the crown of a tooth and/or an attachment positioned on the tooth at one or more points of contact between a tooth receiving cavity of the appliance and received tooth and/or attachment. The magnitude of each of these forces and/or their distribution on the surface of the tooth can determine the type of orthodontic tooth movement which results. Tooth movements may be in any direction in any plane of space, and may comprise one or more of rotation or translation along one or more axes. Types of tooth movements include extrusion, intrusion, rotation, tipping, translation, and root movement, and combinations thereof, as discussed further herein.

Tooth movement of the crown greater than the movement of the root can be referred to as tipping. Equivalent movement of the crown and root can be referred to as translation. Movement of the root greater than the crown can be referred to as root movement.

Figure 3C:
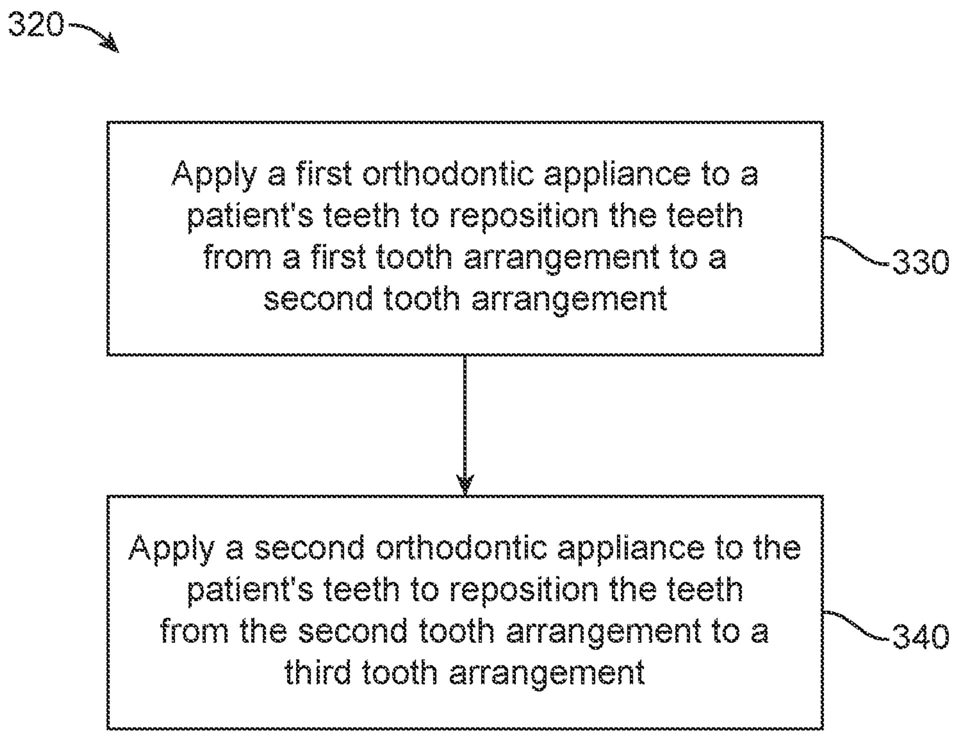
FIG. 3C illustrates a method of orthodontic treatment using a plurality of appliances, in accordance with embodiments.

FIG. 3C illustrates a method 320 of orthodontic treatment using a plurality of appliances, in accordance with embodiments. The method 320 can be practiced using any of the appliances or appliance sets described herein. In step 330, a first orthodontic appliance is applied to a patient's teeth in order to reposition the teeth from a first tooth arrangement to a second tooth arrangement. In step 340, a second orthodontic appliance is applied to the patient's teeth in order to reposition the teeth from the second tooth arrangement to a third tooth arrangement. The method 320 can be repeated as necessary using any suitable number and combination of sequential appliances in order to incrementally reposition the patient's teeth from an initial arrangement to a target arrangement. The appliances can be generated all at the same stage or time point, in sets or batches (e.g., at the beginning of one or more stages of the treatment), or one at a time, and the patient can wear each appliance until the pressure of each appliance on the teeth can no longer be felt or until the maximum amount of expressed tooth movement for that given stage has been achieved. A plurality of different appliances (e.g., a set) can be designed and even fabricated prior to the patient wearing any appliance of the plurality. After wearing an appliance for an appropriate period of time, the patient can replace the current appliance with the next appliance in the series until no more appliances remain. The appliances are generally not affixed to the teeth and the patient may place and replace the appliances at any time during the procedure (e.g., patient-removable appliances). The final appliance or several appliances in the series may have a geometry or geometries selected to overcorrect the tooth arrangement. For instance, one or more appliances may have a geometry that would (if fully achieved) move individual teeth beyond the tooth arrangement that has been selected as the "final." Such over-correction may be desirable in order to offset potential relapse after the repositioning method has been terminated (e.g., permit movement of individual teeth back toward their pre-corrected positions). Over-correction may also be beneficial to speed the rate of correction (e.g., an appliance with a geometry that is positioned beyond a desired intermediate or final position may shift the individual teeth toward the position at a greater rate). In such cases, the use of an appliance can be terminated before the teeth reach the positions defined by the appliance. Furthermore, over-correction may be deliberately applied in order to compensate for any inaccuracies or limitations of the appliance.

Figure 4:
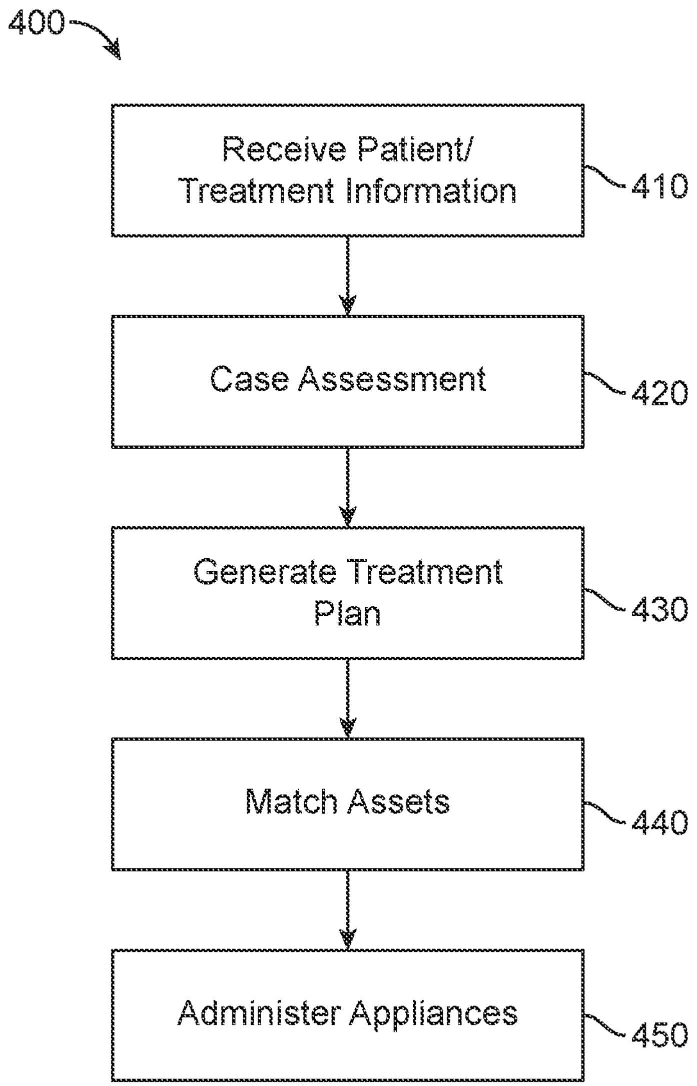
FIG. 4 illustrates a method of treating a patient.

Referring to FIG. 4, a process 400 according to the present disclosure is illustrated. The process 400 includes receiving information regarding the orthodontic condition of the patient and/or treatment information at block 410, generating an assessment of the case at block 420, and generating a treatment plan for repositioning a patient's teeth and block 430. Briefly, patient/treatment information can include obtaining data comprising an initial arrangement of the patient's teeth, which typically includes obtaining an impression or scan of the patient's teeth in their initial positions prior to the onset of treatment and can further include identification of one or more treatment goals selected by the practitioner and/or patient. The patient information can include information such as patient demographic factors, such as age, gender, ethnicity, and race. These factors may help to information the treatment plan because age, gender, and race can all have an impact on how tooth treatment progresses and the effects of treatment. For example, some ages, races, and genders, may respond more or less quickly to certain treatments. Other patient information may include patient tooth factors, such as tooth shape, tooth size, or morphology, arch shape, or cephalometrics, among others. These factors can have an effect on how forces are applied to the teeth, for example, some tooth shapes may not move as desired when force is applied with standard aligners. In such situations attachments may be added to the teeth and attachment receiving wells may be added to the aligners to more effectively impart movement forces onto the patient's tooth.

A case assessment can be generated so as to assess the complexity or difficulty of moving the particular patient's teeth in general or specifically corresponding to identified treatment goals, and may further include practitioner experience and/or comfort level in administering the desired orthodontic treatment. The information and/or corresponding treatment plan will include identifying a final or target arrangement of the patient's teeth that is desired, as well as a plurality of planned successive or intermediary tooth arrangements for moving the teeth along a treatment path from the initial arrangement toward the selected final or target arrangement.

The case assessment and treatment plan may include various treatment strategies, such as staging the movement of teeth in ordered steps to prevent collisions, tooth rotation or translation strategies, interproximal reduction of one or more teeth, and other treatment strategies.

In some embodiments, the treatment strategies are provided by the dental practitioner and the practitioner receives a treatment plan. In some embodiments, the dental practitioner may provide one or more of initial tooth positions, patient information, case assessment information, or dental practitioner information, and receive suggested treatment strategies and a treatment plan based on the information provided.

Figure 5:
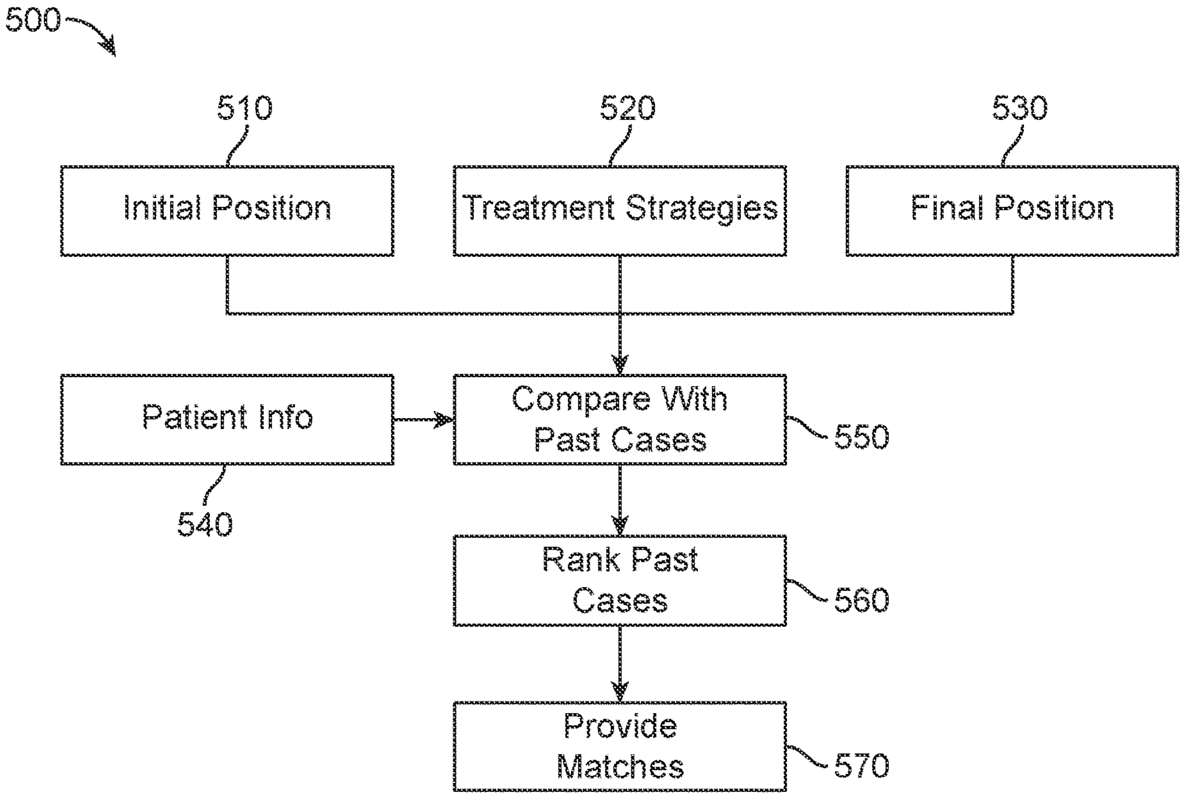
FIG. 5 illustrates a method of matching current cases with existing cases.
Figure 6:
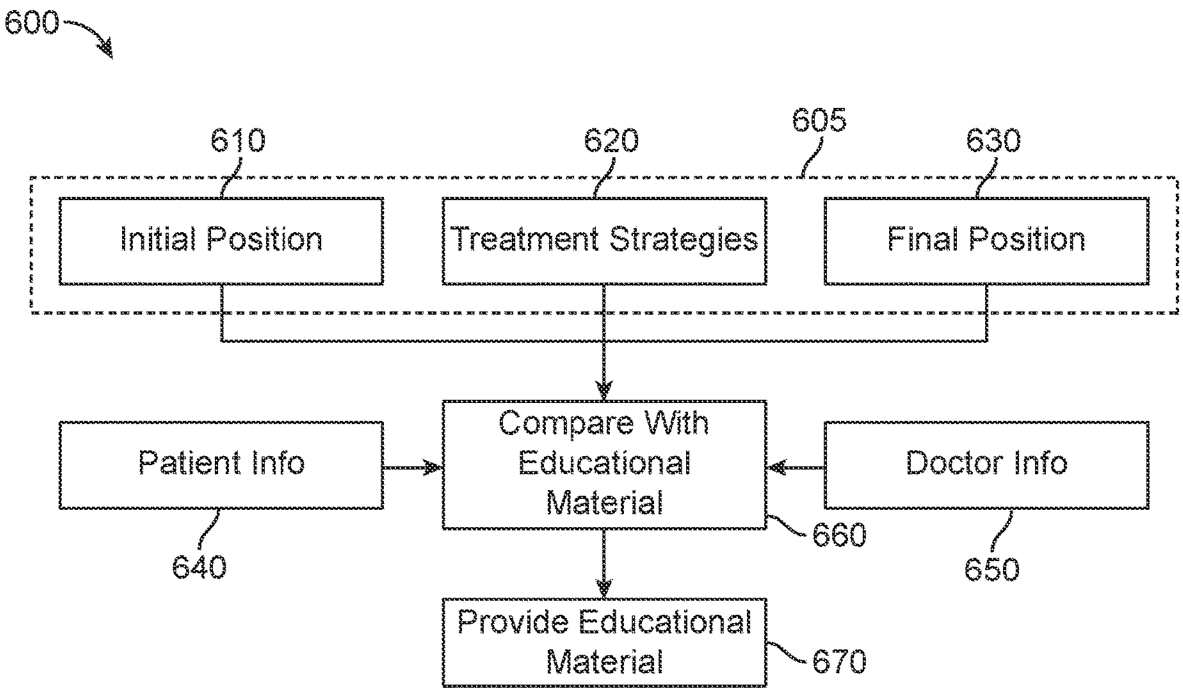
FIG. 6 illustrates a method of matching current cases with educational materials.

As shown in block 440, based on the one or more of the patient and treatment information, the case assessment, or the treatment plan, education and existing cases, including past and presently pending case assets are matched and then provided to the dental practitioner. FIGS. 5 and 6 provide additional details regarding the case and education matching.

As set forth above, appliances can be generated based on sequential planned arrangements of the patient's teeth and can be provided to the practitioner and ultimately administered to the patient at block 450. The appliances are typically provided and/or administered in sets or batches of appliances, such as 2, 3, 4, 5, 6, 7, 8, 9, or more appliances, but are not limited to any particular administrative scheme. Appliances can be provided to the practitioner concurrently with a given set of treatment guidelines, or appliances and guidelines can be provided separately.

Referring to FIG. 5, a method 500 of matching existing cases with a current case is provided. At block 510 an initial position of a patient's teeth for a current case is provided. This can include obtaining data comprising an initial arrangement of the patient's teeth, which typically includes obtaining an impression or scan of the patient's teeth in their initial positions prior to the onset of treatment. In some embodiments, the patient's teeth are scanned directly while in others a mold or impression if formed from the patient's teeth and then the mold is scanned. For example, a plaster cast of the patient's teeth may be made using well known techniques. After the tooth casting is obtained, it can be digitally scanned using a conventional laser scanner or other range acquisition system to produce a digital model or data set of an initial position of the patient's teeth. The data set produced by the range acquisition system may, of course, be converted to other formats to be compatible with the software which is used for manipulating images within the data set. General techniques for producing plaster casts of teeth and generating digital models using laser scanning techniques are well known.

At block 520 treatment strategies for treating a patient's teeth for a current case are provided. The treatment strategies may include, for example, the staging of the movement of teeth in ordered steps to prevent collisions, tooth rotation or translation strategies, interproximal reduction of one or more teeth, and other treatment strategies such as, for example, tooth extraction, elastics use, attachment use, staging, and class II correction. In some embodiments, the treatment strategies may include strategies for treating creation conditions, such as excessive deep bite, open bite, or other conditions.

At block 530 a final or target position of a patient's teeth for a current case is provided. In some embodiments, a target tooth arrangement can be a planned final tooth arrangement selected for the patient's teeth at the end of all planned orthodontic treatment. In some embodiments, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

At block 540 patient information for a current case is provided. The patient information can include information such as patient demographic factors, such as age, gender, and race or patient tooth factors, such as tooth shape, tooth size, or morphology.

At block 550 a comparison is made between one or more of the initial position of a patient's teeth, treatment strategies for treating a patient's teeth, a final position of a patient's teeth, and patient information for a current case and a corresponding one or more of the initial position of a patient's teeth, treatment strategies for treating a patient's teeth, a final position of a patient's teeth, and patient information of a plurality of previous cases.

In some embodiments the degree of matching between the current case information and the case information for each of the plurality of previous cases is determined. In some embodiments, the factors may be binary, wherein a match is made or not made. For example, the sex of the patient may be either male or female and a match is therefore either made or not made depending on the sex of the current patient and the sex of the patient in the existing cases. In some embodiments, a match may be binary even when the factors and not a perfect match. For example, when matching the age of a patient, it may be desirable to include existing cases with patients that are within about 6 months of the age of the current patient or within about 1 year, 2 years, 3 years, or 5 years. In some embodiments an age match may be found when the age of the patient in the existing case is within about 1%, 2%, 5%, or 10% of the age of the current patient.

In some embodiments, a match may be binary based on a threshold. For example, when the position of one or more of the current patient's teeth are within 0.1 mm of the position of one of more of the corresponding teeth of a patient in an existing case, then a match may be made. In some embodiments, a match may be made when the position of one or more of the current patient's teeth are between 0.1 mm and 0.2 mm of the position of one of more of the corresponding teeth of a patient in an existing case or cases. In some embodiments, a match may be made when the position of one or more of the current patient's teeth are less than 0.05 mm, 0.2 mm, 0.3 mm, 0.4 mm, or 0.5 mm of the position of one of more of the corresponding teeth of a patient in an existing case.

In still other embodiments, the match may be a degree or percent match, for example on a scale between a minimum number and a maximum number. For example, with tooth position, a match between the position of a tooth of a current position with the position of a tooth of a past patient of less than 0.01 mm may be considered a 100% match or given a value of 100 (a maximum number), while a position difference of 1 mm or greater may be considered a 0% match or given a value of 0 (a minimum number), and position agreement of between 0.01 mm and 1 mm is assigned a value of between 100% (or 100) and 0% (or 0).

In this way, the information, such as initial position of a patient's tooth, the final position of a patient's tooth, the patient information, and the treatment strategies are compared between the current patient and each of a plurality of existing cases and a degree of match between the cases is assigned to each.

In some embodiments, also at block 550, the degree of match of the information and factors is averaged to determine an overall match for each of the existing cases with the current case.

In some embodiments, each factor or each piece of information, such as initial position of a tooth or set of teeth, the treatment strategies, the final position of a tooth or set of teeth, and the patient information is assigned a relative weight and a weighted average match for each of the existing cases with the current case is determined.

In some embodiments, some existing cases may be dropped from the comparison based on significant mismatch. For example, in some embodiments, only cases of the same sex, cases of adults, cases of teens, or cases of children, may be of interested. In such embodiments, once a mismatch between sex, age, race, etc. is determined, then comparison of that case can end and the case can be dropped from further analysis and ranking.

At block 560 the existing cases are ranked against each other in based on their comparison with the current case. For example, the cases may be ranked from highest to lowest average or weighted average.

In some embodiments, at block 560, the cases may be separated by a particular factor, such as treatment strategy. In such an embodiment, each of the cases may be separately ranked with respect to each treatment strategy.

At block 570 a selection of existing cases are provided to a dental practitioner. In some embodiments, the top 1, 2, 3, 4, or 5 existing cases may be provided to the practitioner based on the average or weighted after degree of match with the present case. In some embodiments, the top 1, 2, 3, 4, or 5, cases for each treatment strategy may be are provided to the practitioner based on the average or weighted after degree of match with the present case for each treatment strategy.

Providing the matched cases may include sending materials or information related to the case to a dental practitioner. For example, the materials for the existing case may include initial scans of the past patient's teeth, final scans of the past patient's teeth, intermediate scans of the past patient's teeth taken during treatment, treatment notes from the treating dental practitioner, and other medical and dental information related to the treatment of the patient in the existing case.

Referring to FIG. 6, a method 600 of matching education materials to a current case is provided. At block 605 case specifics are provided. Case specifics may include the initial position of a patients teeth, a final or target position of a patient's teeth, or treatment strategies proposed by the dental practitioner or a medical device provider, such as a provider of aligners or treatment plans.

At block 610 an initial position of a patient's teeth for a current case is provided. This can include obtaining data comprising an initial arrangement of the patient's teeth, which typically includes obtaining an impression or scan of the patient's teeth in their initial positions prior to the onset of treatment. In some embodiments, the patient's teeth are scanned directly via, for example, an intraoral scan, while in others a mold or impression if formed from the patient's teeth and then the mold is scanned. For example, a plaster cast of the patient's teeth may be made using well known techniques. After the tooth casting is obtained, it can be digitally scanned using a conventional laser scanner or other range acquisition system to produce a digital model or data set of an initial position of the patient's teeth. The data set produced by the range acquisition system may, of course, be converted to other formats to be compatible with the software which is used for manipulating images within the data set. General techniques for producing plaster casts of teeth and generating digital models using laser scanning techniques are well known.

At block 620 treatment strategies for treating a patient's teeth for a current case are provided. The treatment strategies may include, for example, the staging of the movement of teeth in ordered steps to prevent collisions, tooth rotation or translation strategies, interproximal reduction of one or more teeth, and other treatment strategies. In some embodiments, the treatment strategies may include strategies for treating creation conditions, such as excessive deep bite, open bite, or other conditions. In some embodiments the dental practitioner determines and provides the treatment strategies while in other embodiments, a system or medical device provider provides one or more treatment strategies.

At block 630 a final or target position of a patient's teeth for a current case is provided. In some embodiments, a target tooth arrangement can be a planned final tooth arrangement selected for the patient's teeth at the end of all planned orthodontic treatment. In some embodiments, a target arrangement can be one of some intermediate arrangements for the patient's teeth during the course of orthodontic treatment, which may include various different treatment scenarios, including, but not limited to, instances where surgery is recommended, where interproximal reduction (IPR) is appropriate, where a progress check is scheduled, where anchor placement is best, where palatal expansion is desirable, where restorative dentistry is involved (e.g., inlays, onlays, crowns, bridges, implants, veneers, and the like), etc. As such, it is understood that a target tooth arrangement can be any planned resulting arrangement for the patient's teeth that follows one or more incremental repositioning stages. Likewise, an initial tooth arrangement can be any initial arrangement for the patient's teeth that is followed by one or more incremental repositioning stages.

At block 640 patient information for a current case is provided. The patient information can include information such as patient demographic factors, such as age, gender, and race or patient tooth factors, such as tooth shape, tooth size, or morphology.

At block 650 a dental practitioner's information is provided or received. The information may include past training and experience of the dental practitioner. For example, the types of training received and when the training was received, whether the practitioner is a general dental practitioner or a specialist, such as an orthodontist, the educational background of the dental practitioner, the types of cases the dental practitioner has handled the complexities of the cases the dental practitioner has handled, and the number of cases the dental practitioner has handled. In some embodiments, more recent information is proved, such as training received within the last 12 months is provided, while in some embodiments all training is provided.

In some embodiments, the medical equipment the dental practitioner has access to, such as access to an intraoral scanner is received.

In some embodiments, the location of the dental practitioner is received.

In some embodiments, information regarding the dental practitioner's past use of certain tools and resources is received. For example, information regarding the dental practitioner's review of previously provided treatment plans may be considered because, for example, a dental practitioner's interested in reviewing a treatment plan may indicate more advanced knowledge and understand of the tooth repositioning process. In some embodiments, the percentage of cases that are canceled over the lifetime of the dental practitioner or over the last 12 months is received. In some embodiments, the percentage of each type of case put on hold over the lifetime of the dental practitioner or over the last 12 months is received.

At block 660 the provided information and factors are compared and matched with available educational resources. In some embodiments, a dental practitioner's experience with particular procedures or case types is evaluated and if the dental practitioner could use additional educational material when handling such cases, then a match is determined. In some embodiments, educational material matches may be based on the equipment available to the dental practitioner. For example, if the dental practitioner does not have access to an intraoral scanner, then educational material may not be provided for the use of such a device. In some embodiments, education material may be provided for medical equipment not available to the dental practitioner in order to education the dental practitioner on the advantage of using a particular device, such as decreased length of office visits, increased accuracy in evaluating and diagnosing a patient, and other advantages.

In some embodiments, training material is matched to particular patient information, such as the sex, age, or race of the patient because different factors may influence how the patient should be treated and difficulties in treated certain types of patients.

In some embodiments, the case specifics, such as the treatment strategies proposed by the dental practitioner are considered and compared to a set of available treatment strategies for treating a particular condition. One or more of the available treatment strategies may have a high success rate, may be easier to preform, or may be more acceptable to some or a certain class of patients, then education materials directed to one of the other treatment strategies, such as one not selected by the dental practitioner, may be matched.

At block 670 matched educational resources are provided to the dental practitioner. Providing the education resources may include sending materials or information related to the case to a dental practitioner. For example, the materials case studies from existing cases, education materials and training for certain procedures or techniques, or training materials for how to use certain medical equipment or devices. The education resources may be training classes provided in real time to the dental practitioner or video or printed material provided to the dental practitioner.

Figure 7:
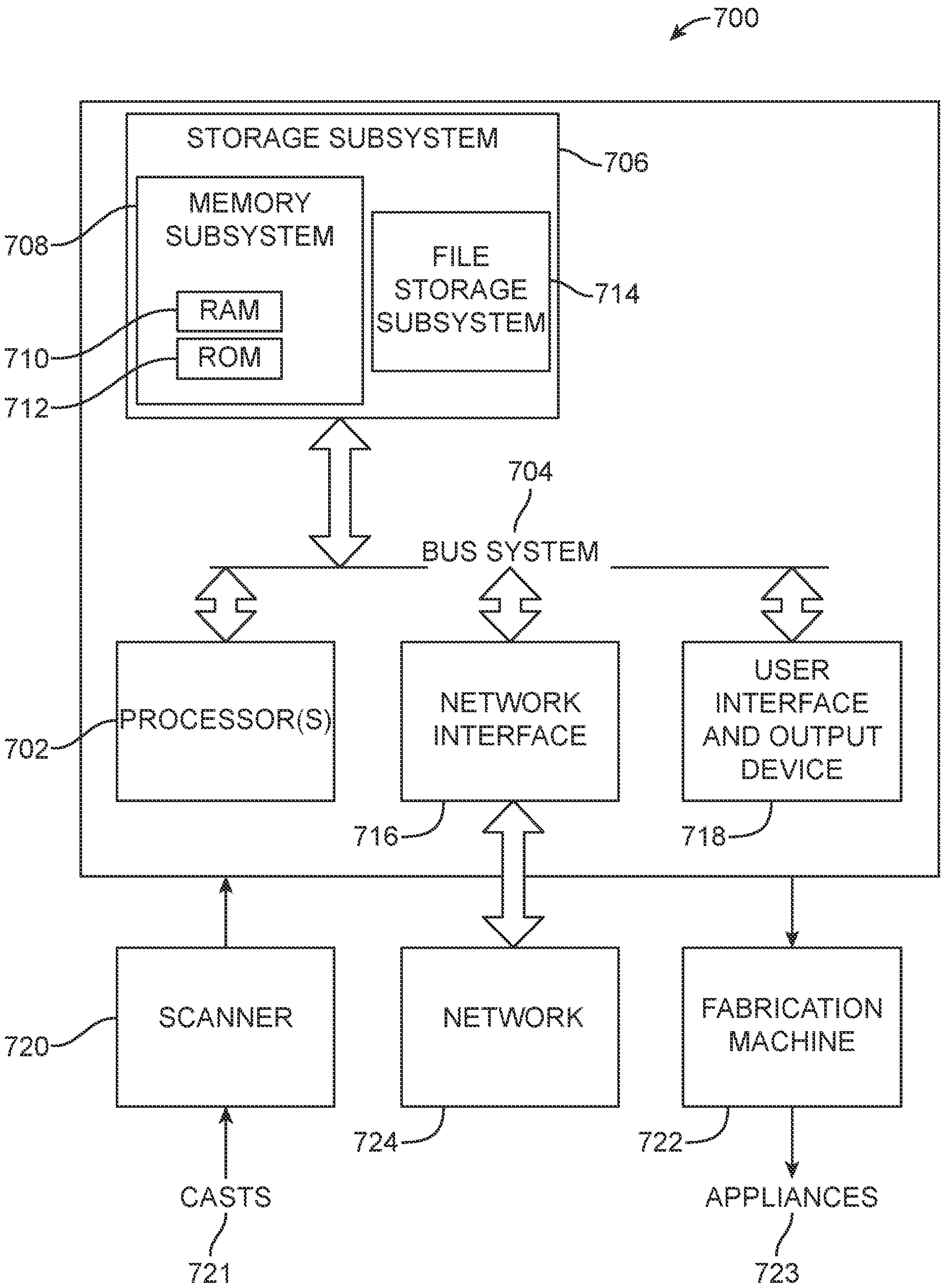
FIG. 7 is a simplified block diagram of a data processing system, in accordance with embodiments.

FIG. 7 is a simplified block diagram of a data processing system 700 that may be used in executing methods and processes described herein. The data processing system 700 typically includes at least one processor 702 that communicates with one or more peripheral devices via bus subsystem 704. These peripheral devices typically include a storage subsystem 706 (memory subsystem 708 and file storage subsystem 714), a set of user interface input and output devices 718, and an interface to outside networks 716. This interface is shown schematically as "Network Interface" block 716, and is coupled to corresponding interface devices in other data processing systems via communication network interface 724. Data processing system 700 can include, for example, one or more computers, such as a personal computer, workstation, mainframe, laptop, and the like.

The user interface input devices 718 are not limited to any particular device, and can typically include, for example, a keyboard, pointing device, mouse, scanner, interactive displays, touchpad, joysticks, etc. Similarly, various user interface output devices can be employed in a system of the disclosure, and can include, for example, one or more of a printer, display (e.g., visual, non-visual) system/subsystem, controller, projection device, audio output, and the like.

Storage subsystem 706 maintains the basic required programming, including computer readable media having instructions (e.g., operating instructions, etc.), and data constructs. The program modules discussed herein are typically stored in storage subsystem 706. Storage subsystem 706 typically includes memory subsystem 708 and file storage subsystem 714. Memory subsystem 708 typically includes a number of memories (e.g., RAM 710, ROM 712, etc.) including computer readable memory for storage of fixed instructions, instructions and data during program execution, basic input/output system, etc. File storage subsystem 714 provides persistent (non-volatile) storage for program and data files, and can include one or more removable or fixed drives or media, hard disk, floppy disk, CD-ROM, DVD, optical drives, and the like. One or more of the storage systems, drives, etc may be located at a remote location, such coupled via a server on a network or via the internet/World Wide Web. In this context, the term "bus subsystem" is used generically so as to include any mechanism for letting the various components and subsystems communicate with each other as intended and can include a variety of suitable components/systems that would be known or recognized as suitable for use therein. It will be recognized that various components of the system can be, but need not necessarily be at the same physical location, but could be connected via various local-area or wide-area network media, transmission systems, etc.

Scanner 720 includes any means for obtaining a digital representation (e.g., images, surface topography data, etc.) of a patient's teeth (e.g., by scanning physical models of the teeth such as casts 721, by scanning impressions taken of the teeth, or by directly scanning the intraoral cavity), which can be obtained either from the patient or from treating professional, such as an orthodontist, and includes means of providing the digital representation to data processing system 700 for further processing. Scanner 720 may be located at a location remote with respect to other components of the system and can communicate image data and/or information to data processing system 1500, for example, via a network interface 724. Optionally, system 700 can include other input sources for obtaining patient data (e.g., CBCT data, ultrasound data, etc.). Fabrication system 722 fabricates appliances 723 based on a treatment plan, including data set information received from data processing system 700. Fabrication machine 722 can, for example, be located at a remote location and receive data set information from data processing system 700 via network interface 724.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

What is claimed is:

1. A method for fabricating an orthodontic appliance to treat malocclusions of a patient's teeth, the method comprising:

receiving a current case information comprising current case factors comprising:

a digital model of an initial topographical information of the patient's teeth, a plurality of treatment strategies for the patient's teeth, patient demographic information, patient tooth information, and a digital model of target positions of the patient's teeth;

comparing pre-existing case information of a plurality of pre-existing cases to the current case information, wherein the pre-existing case information comprises pre-existing case factors comprising:

pre-existing patient demographic information, pre-existing patient tooth information, one or more digital models of initial topographical information of the pre-existing patient's teeth of each of the plurality of pre-existing cases, one or more digital models of target positions of the pre-existing patient's teeth of each of the plurality of pre-existing cases, and a plurality of treatment strategies of the plurality of pre-existing cases;

wherein comparing the current case information to the pre-existing case information further comprises determining a degree of matching between each of the current case factors and one or more of the respective pre-existing case factors of at least a portion of the plurality of pre-existing cases;

determining a subset of the plurality of pre-existing cases, wherein the subset of the plurality of pre-existing cases is based on an average of the degree of matching with the current case information;

generating a digital treatment plan based on the determined subset of the plurality of pre-existing cases, wherein the digital treatment plan prescribes one or more orthodontic appliances configured to move one or more of the patient's teeth from an initial position to a target position corresponding to one or more treatment strategies of the plurality of treatment strategies of the pre-existing case information for the subset of the plurality of pre-existing cases; and fabricating, by a fabrication machine, the one or more orthodontic appliances based on the digital treatment plan.

2. The method of claim 1, wherein the current case factors further comprise one or more digital models of initial root positions of the patient's teeth, target root positions of the patient's teeth, or both.

3. The method of claim 1, wherein the method further comprises providing to a dental practitioner a selection of educational material, wherein the educational material is selected based on the selection of pre-existing cases.

4. The method of claim 1, further comprising ranking the subset of the plurality of pre-existing cases based on the degree of pre-existing case factor matching.

5. The method of claim 4, wherein the degree of matching with the current case information of the subset of the plurality of the pre-existing cases is above a predetermined threshold.

6. The method of claim 1, the method further comprising removing one or more pre-existing cases from the plurality of existing cases.

7. The method of claim 6, further comprising removing the one or more pre-existing cases based at least in part on a mismatch of the one or more pre-existing case factors with the one or more current case factors.

8. The method of claim 1, wherein the patient demographic information comprises one or more of age, sex, ethnicity, and race.

9. The method of claim 1, wherein the patient tooth information comprises one or more of tooth shape, tooth size, tooth morphology, and arch shape.

10. The method of claim 1, wherein the target position represents a desired position of the patient's teeth at completion of treatment.

11. The method of claim 1, wherein the target position represents an intermediate position of the patient's teeth during treatment.

12. The method of claim 11, wherein the treatment further comprises interproximal reduction.

13. The method of claim 11, wherein the treatment further comprises restorative dentistry.

14. The method of claim 1, the method further comprising:

generating a plurality of intermediate tooth arrangements for moving the patient's teeth along a treatment path from the initial position toward the target position in the digital treatment plan; and providing the digital treatment plan to a dental practitioner.

15. The method of claim 1, wherein the one or more pre-existing case factors further comprise one or more digital models of initial positions of the pre-existing patient's teeth.

16. The method of claim 1, wherein the subset of the plurality of pre-existing cases comprises one or more pre-existing case factors matched to a current case factor with a high average degree of matching.

17. The method of claim 1, wherein the degree of matching between each of the current case factors and one or more of the respective pre-existing case factors of the at least portion of the plurality of pre-existing cases is based at least in part on a relative weight value of the current case factor that is matched to the one or more respective pre-existing case factors.

18. The method of claim 1, wherein the pre-existing patient demographic information comprises one or more of age, sex, ethnicity, and race.

19. The method of claim 1, wherein the pre-existing patient tooth information comprises one or more of tooth shape, tooth size, tooth morphology, and arch shape.

* * * * *